US012562078B2

(12) United States Patent
Isaacson et al.

(10) Patent No.: US 12,562,078 B2
(45) Date of Patent: Feb. 24, 2026

(54) VEIN SIMULATOR SYSTEM

(71) Applicant: Becton, Dickinson and Company,
Franklin Lakes, NJ (US)

(72) Inventors: S. Ray Isaacson, Layton, UT (US);
Weston F. Harding, Lehi, UT (US);
Aaron Bell-Cares, Mapleton, UT (US);
Nathan Christiansen, Spanish Fork,
UT (US); Brenda Williams, Holbrook,
AZ (US); Caleb Larson, Tucson, AZ
(US); Ross Knutson, Cheney, WA
(US); Alyson Devenport, Salem, UT
(US); Dorothy Taylor, Springville, UT
(US)

(73) Assignee: Becton, Dickinson and Company,
Franklin Lakes, NJ (US)

( * ) Notice: Subject to any disclaimer, the term of this
patent is extended or adjusted under 35
U.S.C. 154(b) by 871 days.

(21) Appl. No.: 17/731,107

(22) Filed: Apr. 27, 2022

(65) Prior Publication Data

US 2022/0383777 A1    Dec. 1, 2022

Related U.S. Application Data

(60) Provisional application No. 63/194,394, filed on May
28, 2021.

(51) Int. Cl.
*G09B 23/30*        (2006.01)
*A61B 5/00*         (2006.01)
(Continued)

(52) U.S. Cl.
CPC .......... *G09B 23/285* (2013.01); *A61B 5/0084*
(2013.01); *G09B 23/34* (2013.01)

(58) Field of Classification Search
CPC ...... G09B 23/28; G09B 23/285; G09B 23/30;
G09B 23/303
See application file for complete search history.

(56) References Cited

U.S. PATENT DOCUMENTS 3,520,071 A * 7/1970 Clark ..................... G09B 23/32
                                                434/265
4,182,054 A * 1/1980 Wise .................... G09B 23/285
                                                434/272
(Continued)

FOREIGN PATENT DOCUMENTS

EP        3399515 A1    11/2018
EP        3613033 A1    2/2020
(Continued)

*Primary Examiner* — Kurt Fernstrom
(74) *Attorney, Agent, or Firm* — Kirton McConkie;
Whitney Blair; Kevin Stinger

(57)        ABSTRACT

A vein simulator system can be used by clinicians to
improve their proficiency in placing catheters such as PIVCs
or in otherwise accessing a vasculature. A vein simulator
system can include a simulated portion of a body, such as a
simulated human arm, that includes at least one simulated
vein. The vein simulator system can also include a control
system, one or more sensors and one or more feedback
components. The control system can leverage the one or
more sensors to generate feedback during a clinician's
attempt to place a catheter and can output the feedback via
the feedback components, either during or after the attempt.

20 Claims, 9 Drawing Sheets

(51) Int. Cl.
    *G09B 23/28*       (2006.01)
    *G09B 23/34*       (2006.01)

(56)          References Cited

U.S. PATENT DOCUMENTS

| | | | | |
|---|---|---|---|---|
| 5,215,469 | A * | 6/1993 | Kohnke | G09B 23/285 |
| | | | | 434/272 |
| 6,470,302 | B1 | 10/2002 | Cunningham et al. | |
| 6,773,263 | B2 * | 8/2004 | Nicholls | G09B 23/30 |
| | | | | 434/272 |
| 7,731,500 | B2 * | 6/2010 | Feygin | G09B 23/285 |
| | | | | 434/262 |
| 8,556,635 | B2 * | 10/2013 | Toly | G09B 23/285 |
| | | | | 434/262 |
| 8,784,111 | B2 * | 7/2014 | Feygin | G09B 23/285 |
| | | | | 434/262 |
| 12,070,581 | B2 * | 8/2024 | Rios | A61M 5/3135 |
| 2003/0068606 | A1 * | 4/2003 | Nicholls | G09B 23/34 |
| | | | | 434/262 |
| 2009/0208915 | A1 * | 8/2009 | Pugh | G09B 23/30 |
| | | | | 434/270 |
| 2012/0045742 | A1 | 2/2012 | Meglan et al. | |
| 2012/0100515 | A1 | 4/2012 | Hungness et al. | |
| 2013/0052626 | A1 * | 2/2013 | Hoskins | G09B 23/285 |
| | | | | 434/268 |
| 2013/0078603 | A1 * | 3/2013 | Yang | G09B 23/285 |
| | | | | 434/268 |
| 2013/0288218 | A1 * | 10/2013 | Mallin | G09B 23/303 |
| | | | | 434/268 |
| 2014/0329215 | A1 * | 11/2014 | Pugh | G09B 23/30 |
| | | | | 434/267 |
| 2015/0064675 | A1 * | 3/2015 | Eichhorn | A61B 17/29 |
| | | | | 434/262 |
| 2017/0011658 | A1 * | 1/2017 | Ozaki | G09B 23/30 |
| 2017/0263158 | A1 * | 9/2017 | East | B29C 45/14795 |
| 2019/0027066 | A1 | 1/2019 | Altermatt Couratier et al. | |
| 2019/0385485 | A1 | 12/2019 | Walker et al. | |
| 2020/0126449 | A1 * | 4/2020 | Horst | G09B 23/285 |
| 2020/0152091 | A1 * | 5/2020 | Haga | G09B 23/285 |
| 2020/0365057 | A1 * | 11/2020 | Fernandez | G09B 23/303 |
| 2023/0037923 | A1 * | 2/2023 | Desmet | A61B 8/4245 |

FOREIGN PATENT DOCUMENTS

| | | |
|---|---|---|
| JP | 2002502058 A | 1/2002 |
| KR | 10-1317860 B1 | 10/2013 |
| WO | 2016028821 A1 | 2/2016 |
| WO | 2017113022 A1 | 7/2017 |
| WO | 2018195178 A1 | 10/2018 |

* cited by examiner

132/142     115     211  210                      130

131/141

116/122                                          141a

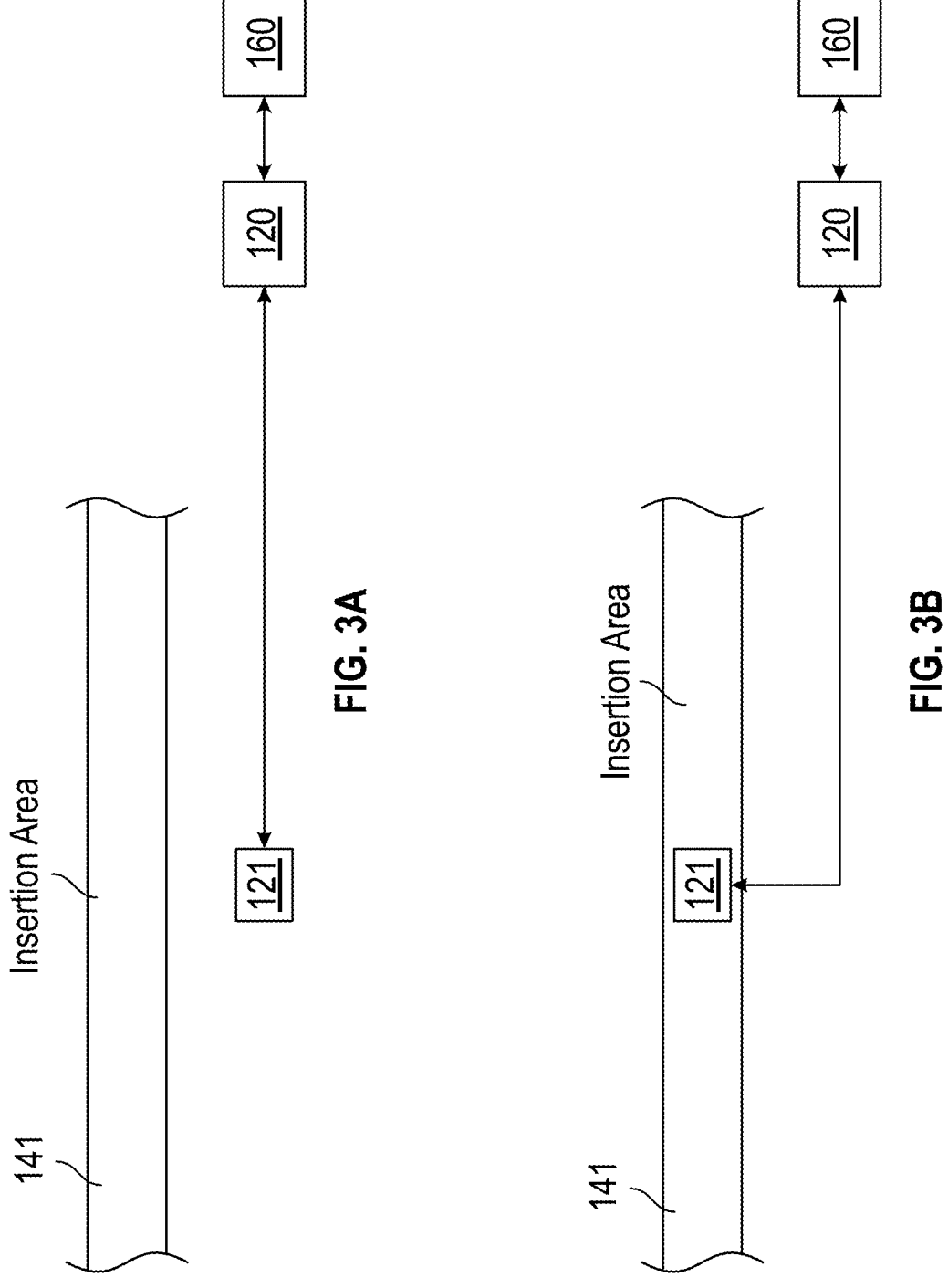

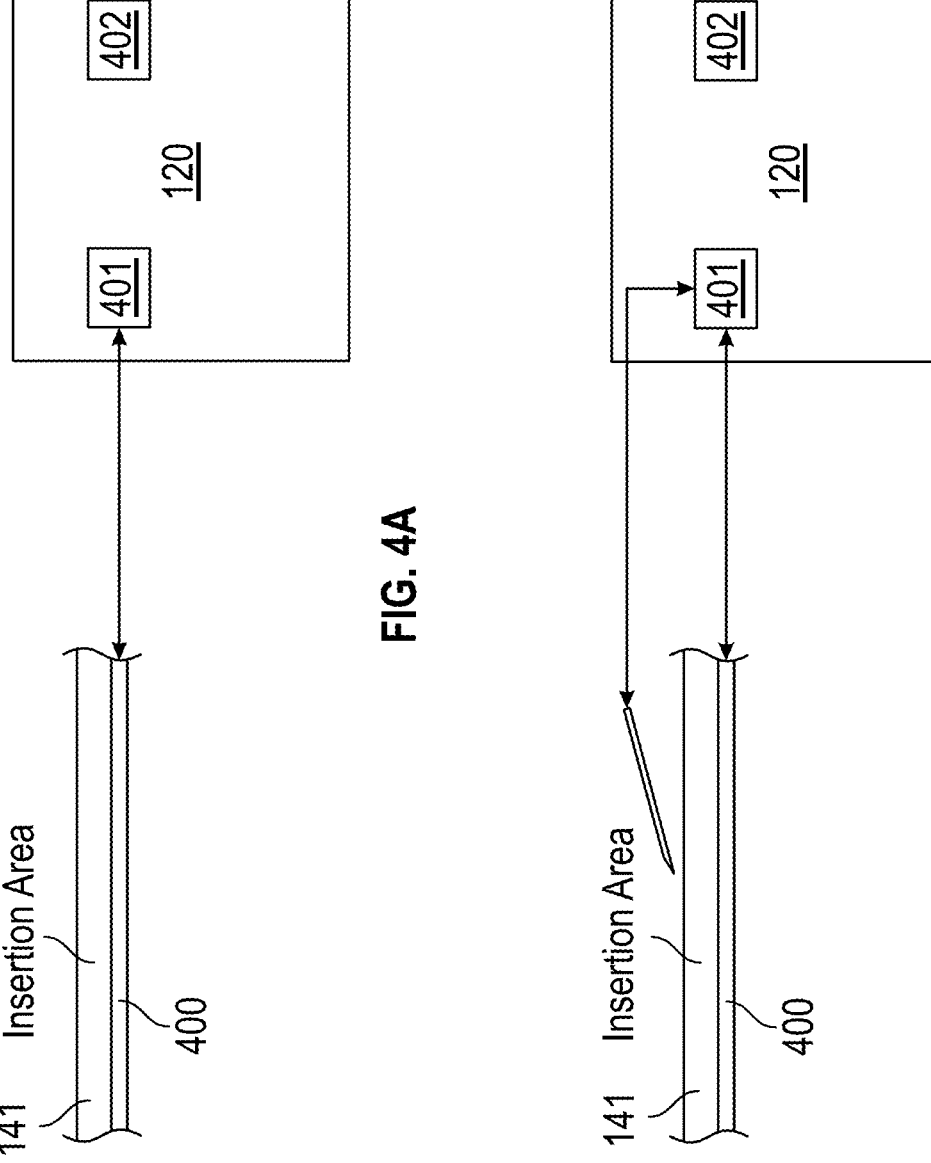

VEIN SIMULATOR SYSTEM

RELATED APPLICATIONS

This application claims the benefit of U.S. Provisional Patent Application No. 63/194,394, filed on May 28, 2021, entitled VEIN SIMULATOR SYSTEM, which is incorporated herein in its entirety.

BACKGROUND

When clinicians such as nursing students graduate, they typically have a minimal level of proficiency in placing peripheral intravenous catheters (PIVCs) and are expected to gain proficiency on the job. A problem with this approach is that an inexperienced clinician will oftentimes require multiple attempts to successfully place a PIVC—an experience that is not pleasant for the patient. To minimize negative experiences, many facilities limit the number of failed attempts an inexperienced clinician can make. After the inexperienced clinician reaches the maximum allowed number of failed attempts (e.g., two), an experienced clinician will be required to place the PIVC.

Some vein simulators have been developed to allow inexperienced clinicians to improve their proficiency in placing PIVCs. Such vein simulators are oftentimes in the form of a fake arm containing a tube through which red fluid is pumped. These vein simulators may be made of materials that respond similar to human skin and veins and may therefore allow an inexperienced clinician to learn how it should feel when the needle pierces the vein during placement of a PIVC. However, these vein simulators do not provide useful guidance for teaching the inexperienced clinician when he or she has properly or improperly placed the PIVC.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to a vein simulator system that can be used by clinicians to improve their proficiency in placing catheters such as PIVCs or in otherwise accessing a vasculature. A vein simulator system can include a simulated portion of a body, such as a simulated human arm, that includes at least one simulated vein. The vein simulator system can also include a control system, one or more sensors and one or more feedback components. The control system can leverage the one or more sensors to generate feedback during a clinician's attempt to place a catheter and can output the feedback via the feedback components, either during or after the attempt.

In some embodiments, a vein simulator system may include a simulated portion of a body that includes a first simulated vein, a control system, at least one sensor and at least one feedback component. The control system may be configured to employ the at least one sensor to create feedback while a clinician attempts to place a catheter in the first simulated vein. The control system may be further configured to present the feedback to the clinician via the at least one feedback component.

In some embodiments, the simulated portion of the body is a simulated human arm. In some embodiments, the at least one sensor includes one or more cameras. In some embodiments, the at least one feedback component includes a display device. In some embodiments, the camera is external to the simulated portion of the body. In some embodiments, the simulated portion of the body includes simulated inner tissue within which the first simulated extends and the camera is positioned within to the simulated inner tissue. In some embodiments, the camera is positioned inside the first simulated vein.

In some embodiments, the simulated portion of the body includes simulated inner tissue and the vein simulator system further includes a light source that illuminates the simulated inner tissue. In some embodiments, the at least one sensor includes a film that is on or forms part of a sidewall of the simulated vein. In some embodiments, the control system creates the feedback based on a signal created, induced or conveyed by the film in response to proximity or contact of a needle used to place the catheter. In some embodiments, the at least one feedback component includes an audio feedback component or a visual feedback component. In some embodiments, the at least one sensor comprises multiple sensors, and the control system is configured to create an association between feedback generated by the multiple sensors.

In some embodiments, a vein simulator system may include a simulated portion of a body that includes simulated inner flesh, a first simulated vein that extends within the simulated inner flesh and simulated skin that is positioned overtop the simulated inner flesh and the first simulated vein. The vein simulator system may further include a control system and at least one camera that is positioned to capture video of the first simulated vein.

In some embodiments, the at least one camera may be positioned outside the simulated inner flesh, positioned inside the simulated inner flesh and/or positioned inside the first simulated vein. In some embodiments, the vein simulator system may include at least one sensor positioned on or in a sidewall of the first simulated vein, and the at least one sensor may be configured to provide to the control system an indication of when a needle contacts or is proximate to the sensor. In some embodiments, the vein simulator system may include at least one feedback component. In some embodiments, the at least one feedback component may be one or more of a display device, a speaker or a light.

In some embodiments, a vein simulator system may include a simulated portion of a body that includes a first simulated vein, a pump for pumping fluid through the first simulated vein, a control system, at least one sensor and at least one feedback component. In some embodiments, the control system may be configured to use the at least one sensor to generate feedback while a clinician attempts to place a catheter in the first simulated vein, and may be configured to output the feedback via the at least one feedback component.

It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 3A is a block diagram representing how a vein simulator system that is configured in accordance with one or more embodiments of the present disclosure can employ a camera that is external to a simulated vein to provide visual feedback during placement of a PIVC;

FIG. 3B is a block diagram representing how a vein simulator system that is configured in accordance with one or more embodiments of the present disclosure can employ a camera that is internal to a simulated vein to provide visual feedback during placement of a PIVC; and FIGS. 4A and 4B are each a block diagram representing how a vein simulator system that is configured in accordance with one or more embodiments of the present disclosure can employ a sensor on or within a simulated vein to provide feedback during placement of a PIVC.

DESCRIPTION OF EMBODIMENTS

Figure 1A:
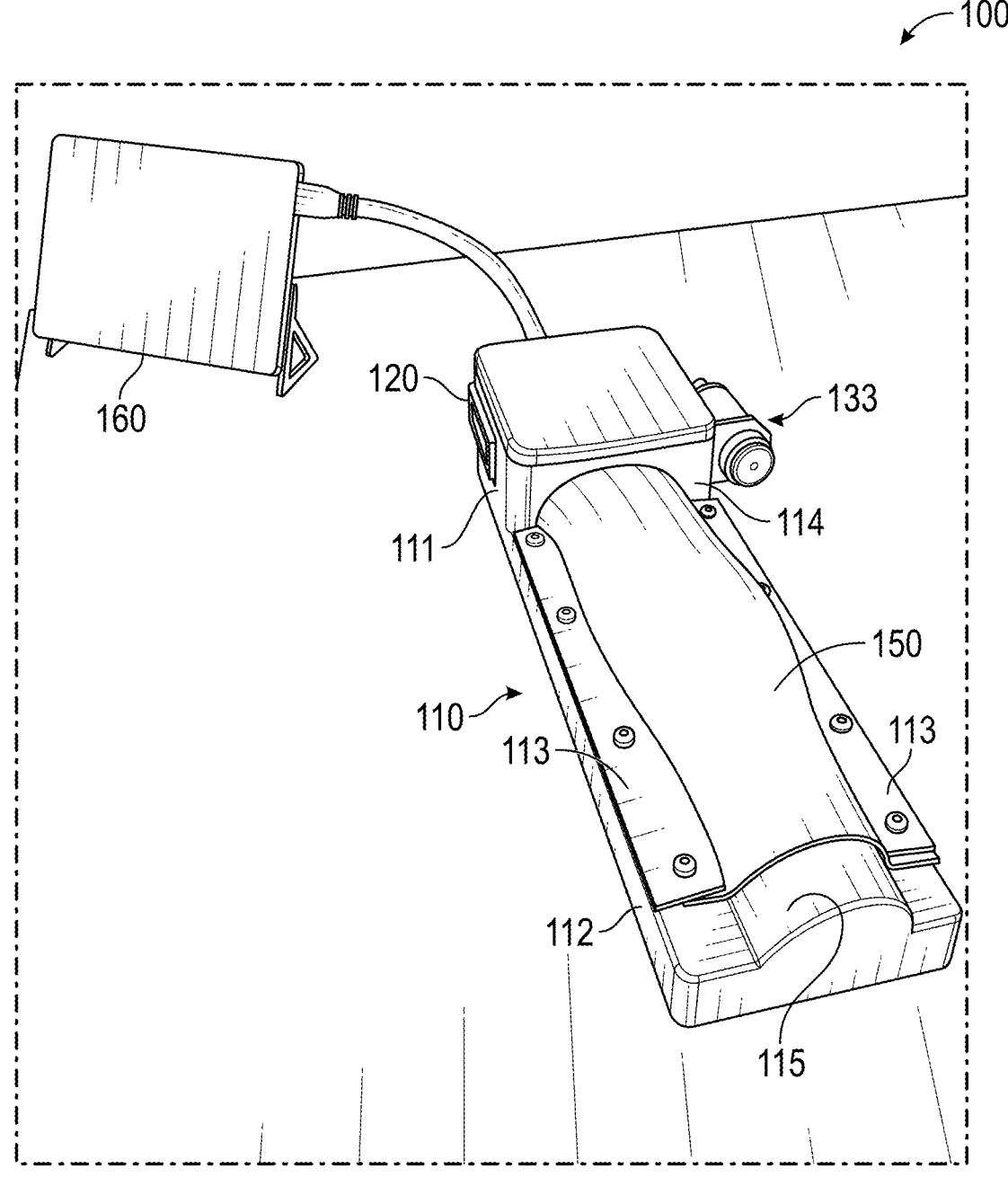
FIG. 1A is an assembled view of a vein simulator system that is configured in accordance with one or more embodiments of the present disclosure.
Figure 1B:
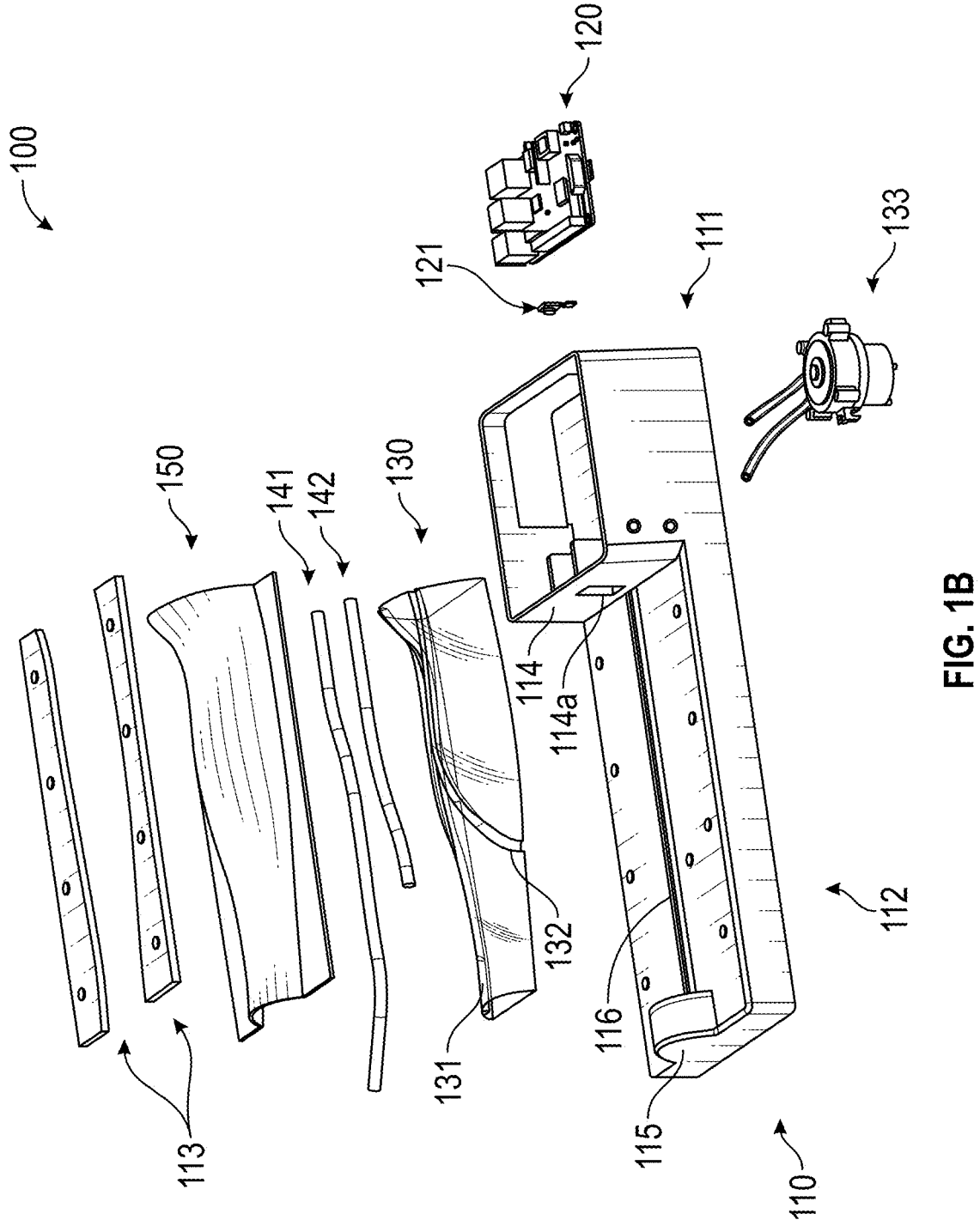
FIG. 1B is a disassembled view of the vein simulator system of FIG. 1A.
Figure 1C:
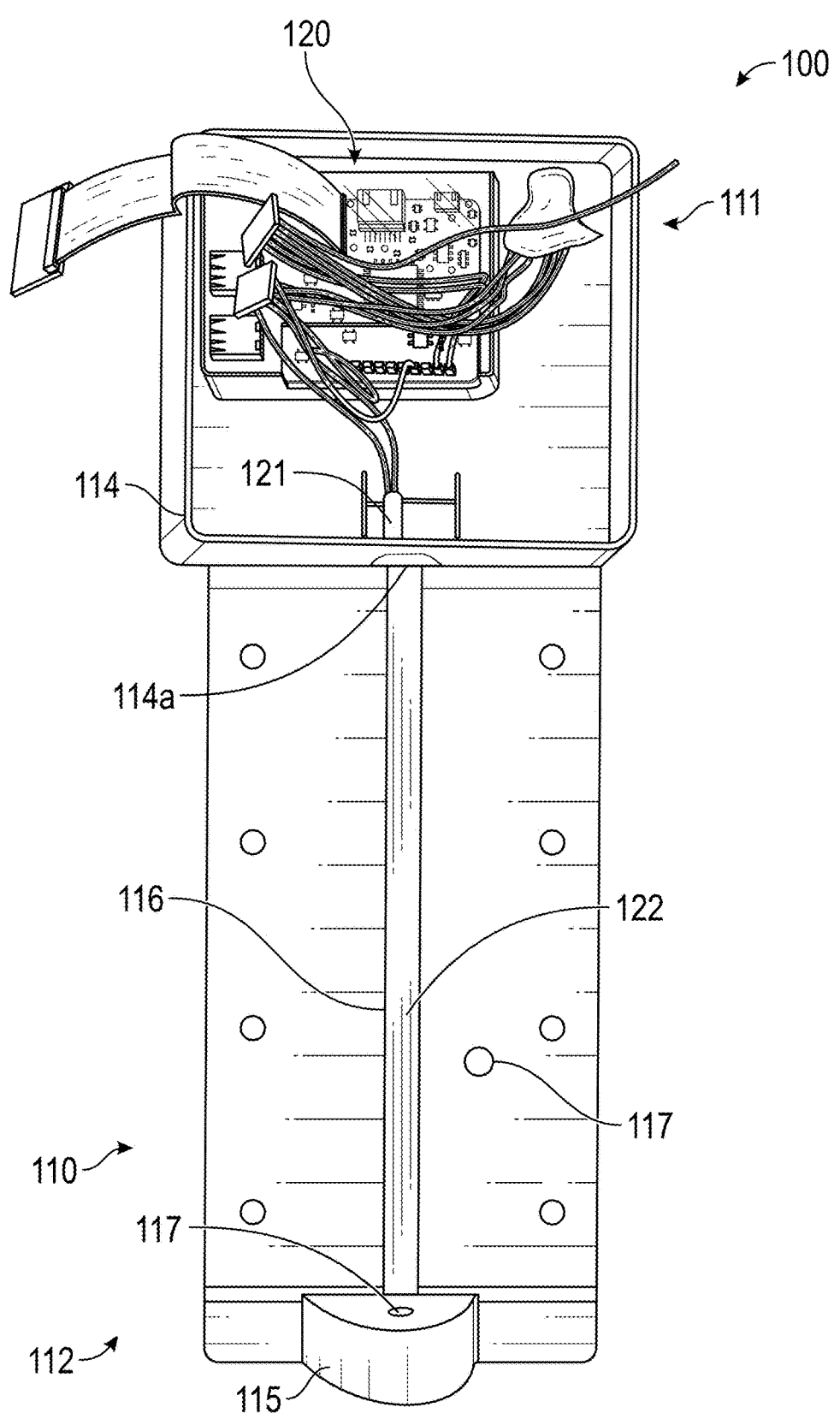
FIG. 1C shows the vein simulator system of FIG. 1A with the simulated arm removed.

A vein simulator system that is configured in accordance with one or more embodiments of the present disclosure can employ one or more sensors to provide feedback to a clinician during the process of placing a PIVC. Different types of sensors may be employed to provide different types of feedback. For example, a camera may be employed to provide visual (e.g., video) feedback of the advancement of the PIVC within a simulated vein. As another example, a film, such as a conductive or capacitive material, may be included on, within or near a simulated vein to provide visual and/or audio feedback representing the position of the PIVC within a simulated vein.

FIGS. 1A-1E provide an example of a vein simulator system 100 that is configured in accordance with one or more embodiments of the present disclosure. Vein simulator system 100 includes a base 110 having a housing 111 and a support 112. Housing 111 can primarily be used to house various computing, electrical or other components, while support 112 can primarily be used to support a simulated arm or other simulated portion of a human body or animal.

In some embodiments, a simulated arm or other simulated portion can be formed of simulated inner tissue 130 (e.g., medical gelatin) which may include a number of channels (e.g., channels 131 and 132) for receiving simulated veins (e.g., simulated veins 141 and 142 which may be formed of rubber latex tubing in some embodiments) and simulated skin 150 (e.g., a silicone-based material with a single outer layer of a spandex powermesh fabric) for covering simulated inner tissue 130. Simulated inner tissue 130 can be positioned on top of support 112 and simulated skin 150 can be placed overtop simulated inner tissue 130 and secured to support 112 via securing members 113. For example, as best seen in FIG. 1E, support 112 may include holes 118 for receiving screws 119 which tighten securing member 113 overtop the sides of simulated skin 150. Screws 119 may insert through simulated skin 150 to ensure that simulated skin 150 is held tightly overtop simulated inner tissue 130. As other examples, springs, loaded clamps, snap members, or any other suitable mechanism could be used to secure securing member 113 to support 112.

Simulated veins 141 and 142 can be positioned in channels 131 and 132 and connected together at one end and connected to pump 133 at the opposite end to thereby enable pump 133 to cause simulated to flow through simulated veins 141 and 142. In some embodiments, support 112 can be at least partially hollow to allow the ends of simulated veins 141 and 142 to be connected (e.g., via tubing that extends between holes 117 in support 112 and protruding end 115. In some embodiments, a single length of tubing could be used to form simulated veins 141 and 142. In some embodiments, channels 131 and 132 and simulated veins 141 and 142 may be sized and configured in an anatomically correct manner (e.g., to match the size and position of veins in an actual human arm). However, any configuration of channel(s) and simulated vein(s) could be used in embodiments.

Vein simulator system 100 may also include a control system 120 (e.g., a computer) that can be housed within housing 111. In some embodiments, control system 120 may power pump 133 to ensure that fluid pressure and fluid flow within simulated veins 141 and 142 matches a desired blood pressure and rate of blood flow. In some embodiments, control system 120 may power/control a light source 122 that may be positioned under or within simulated inner tissue 130. For example, support 112 may include a channel 116 within which light source 122 may be housed. In some embodiments, light source 122 may be in the form of an LED strip. In some embodiments, light source 122 may extend along the full length of simulated inner tissue 130 or along a portion of the length of simulated inner tissue 130 (e.g., under an intended insertion site).

Figure 1D:
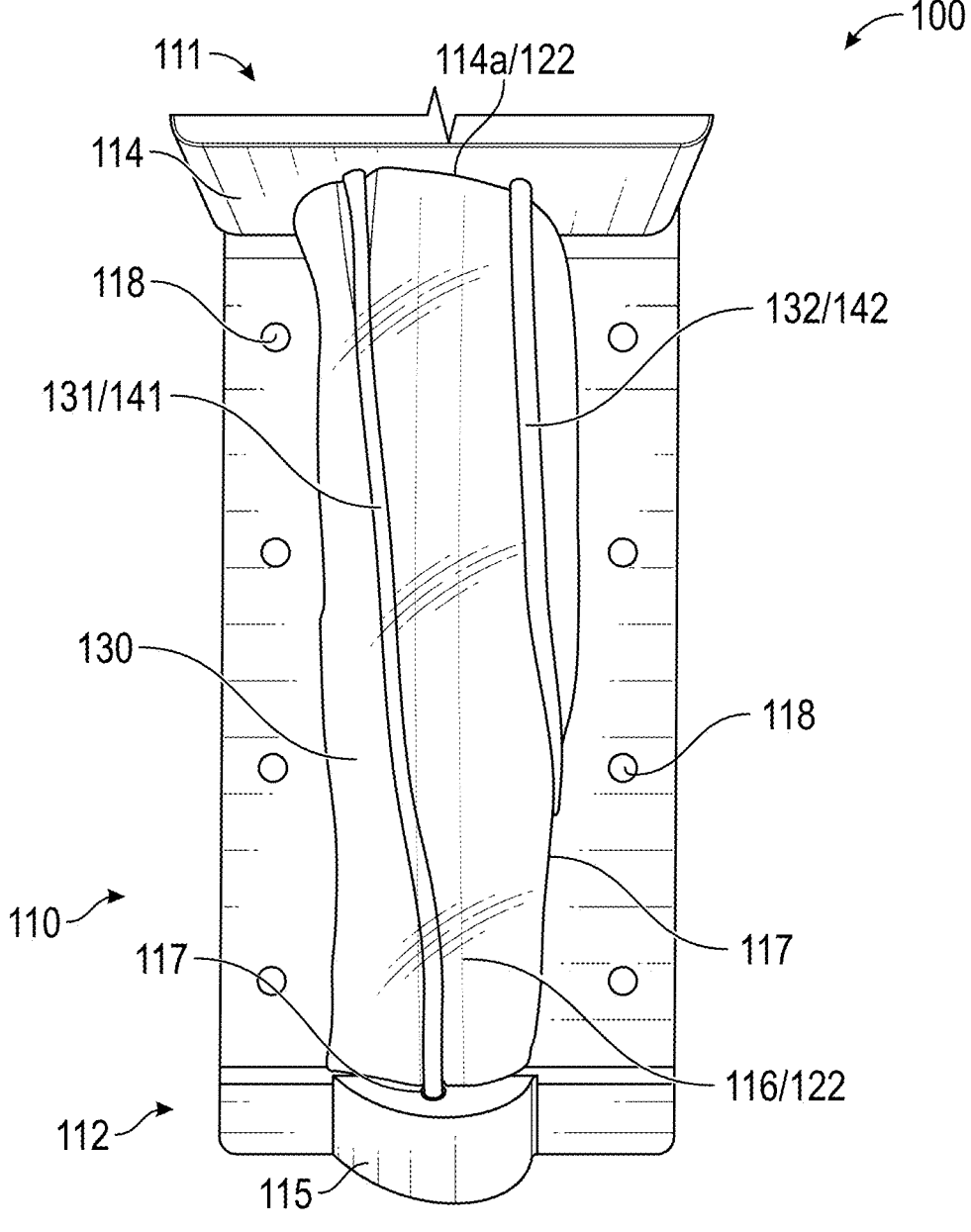
FIG. 1D shows the vein simulator system of FIG. 1A with the simulated skin removed from the simulated arm.
Figure 1E:
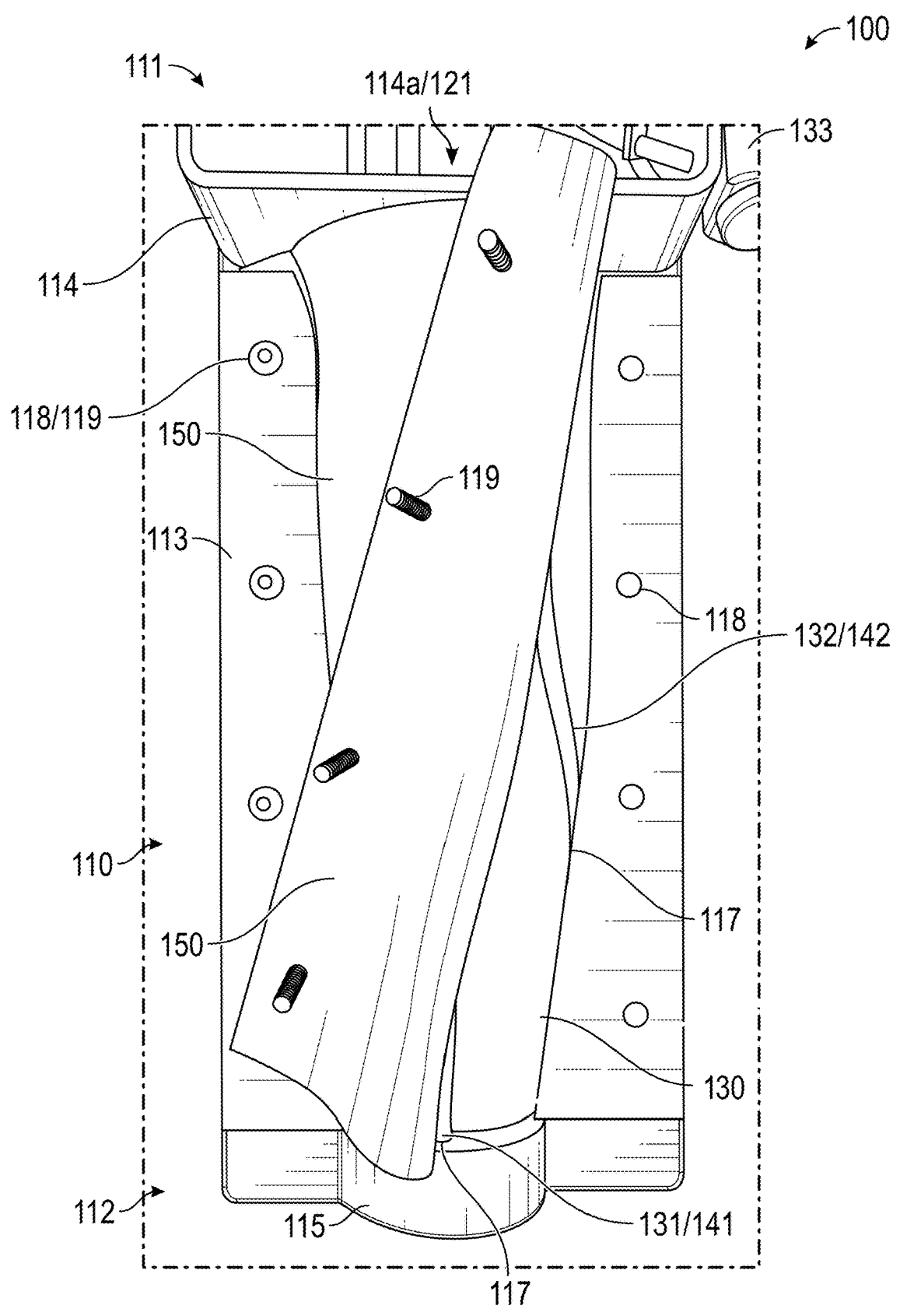
FIG. 1E shows the vein simulator system of FIG. 1A with the simulated skin partially removed from the simulated arm.

As best seen in FIG. 1D, in some embodiments, simulated inner tissue 130 may be transparent such that light source 122 may illuminate it and allow camera 121 (which is one type of sensor that may be employed in embodiments of the present disclosure) to capture video of simulated inner tissue 130 (which is a visual type of feedback that may be provided in embodiments of the present disclosure). For example, housing 111 may include a wall 114 that faces simulated inner tissue 130 and includes an opening 114a. Camera 121 may be placed in opening 114a and directed towards simulated inner tissue 130. Control system 120 may then use camera 121 to capture video of simulated inner tissue 130 and simulated veins 141 and 142 while a clinician practices placing a PIVC. In some embodiments, vein simulator system 100 may include a display device 160 that may be coupled to control system 120 to thereby enable control system 120 to output the video to display device 160. Accordingly, the clinician can watch the video on display device 160 as his or she attempts to place the PIVC.

Simulated inner tissue 130, simulated veins 141 and 142 and simulated skin 150 can be designed to have mechanical properties matching those of a human arm. For example, by configuring simulated skin 150 from a silicone-based material having an outer layer of a spandex powermesh fabric and by configuring simulated veins 141 and 142 of rubber latex tubing, the penetration force and stiffness can substantially match the penetration force and stiffness of human skin and veins. Also, simulated veins 141 and 142 can be sized and positioned to match the size and position of human veins. Pump 133 can be configured to create fluid pressure within simulated veins 141 and 142 matching human blood pressure thereby creating a realistic flashback when simulated veins 141 and 142 are punctured. Further, by forming simulated inner tissue 130 of medical gelatin, it can provide support and consistency similar to human subcutaneous tissue while being transparent to facilitate viewing the insertion site as described below. In some embodiments, a heat gun can be used on simulated inner tissue 130 after it is molded into shape to increase its transparency. In some embodiments, a flat piece of glass or clear plastic may be pressed against simulated inner tissue 130 to flatten its surface and remove optical distortions caused by any unevenness of the surface.

Figure 2A:
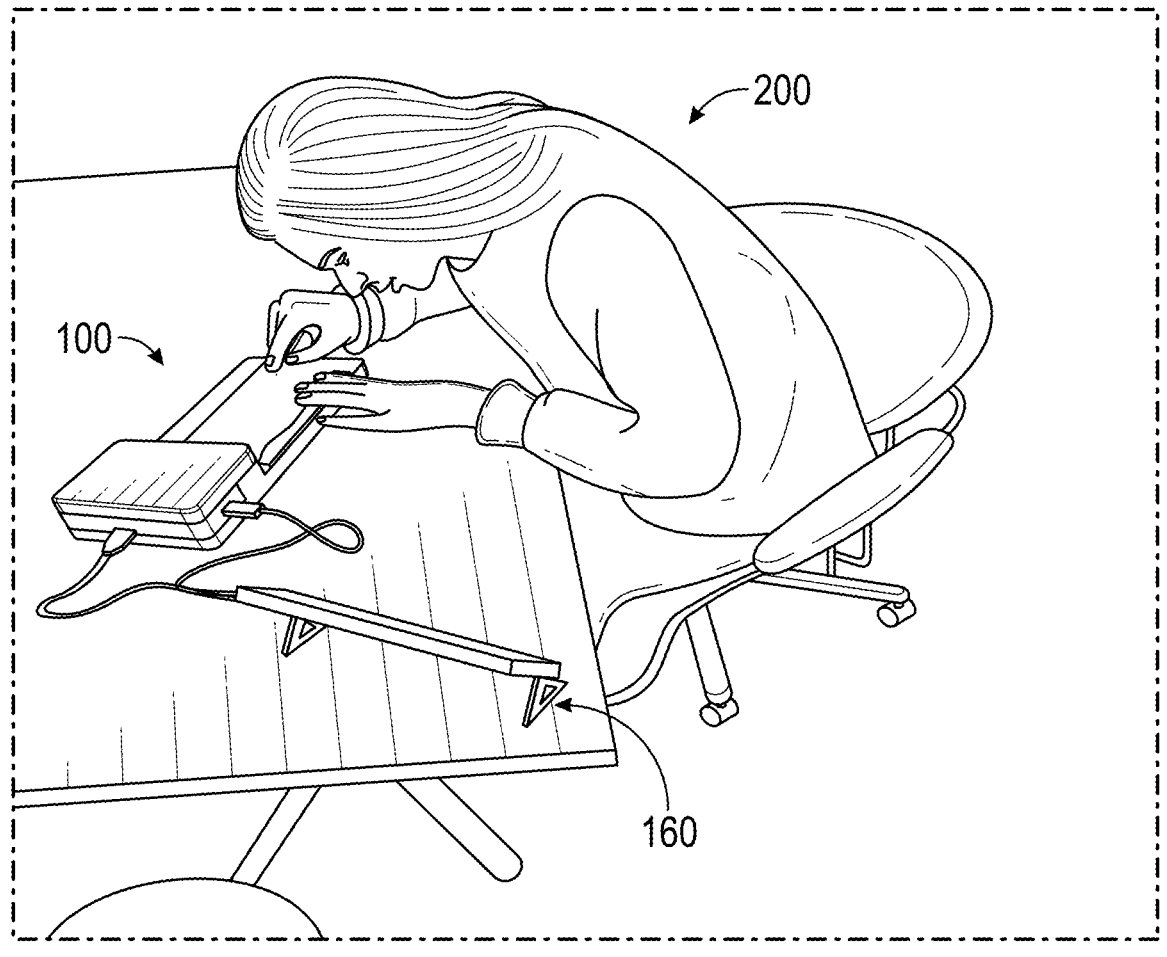
FIG. 2A shows a clinician using the vein simulator system of FIG. 1A.
Figure 2B:
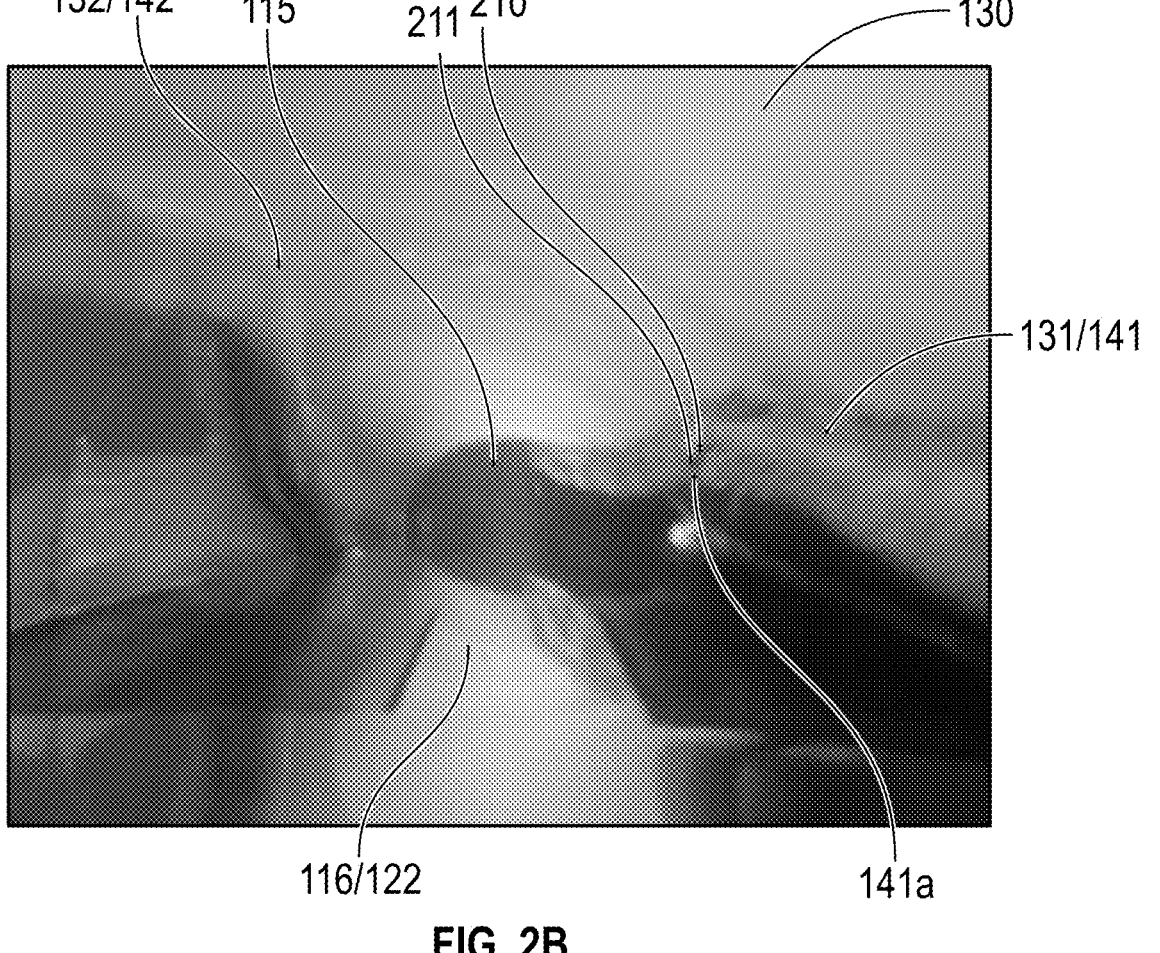
FIG. 2B provides an example of visual feedback that may be provided during placement of a PIVC by the vein simulator system of FIG. 1A or another vein simulator system that is configured in accordance with one or more embodiments of the present disclosure.

FIGS. 2A and 2B provide an example of how vein simulator system 100 may allow a clinician to watch video of his or her attempt to place a PIVC. FIG. 2A shows a clinician 200 attempting to place a PIVC into simulated vein 141. FIG. 2B provides an example of the video that camera 121 may capture and that may be displayed on display device 160 during this attempt. As shown, light source 122 in channel 116 illuminates simulated inner tissue 130 including channels 131 and 132 and simulated veins 141 and 142 contained therein. With this illumination, needle 210 and the distal tip 211 of needle 210 can be seen. In particular, the video enables the clinician to see the position of distal tip 211 relative to the sidewall 141a of simulated vein 141. In this context, the sidewall can be viewed as a wall of simulated vein 141 that is opposite the point of insertion and may typically be the bottom wall of simulated vein 141.

By viewing the video, whether during or after placing the PIVC, the clinician can learn whether he or she successfully placed the PIVC. For example, the visual feedback that camera 121 provides can help the clinician learn when distal tip 211 of needle 210 has reached the proper position within simulated vein 141. This can assist the clinician, not only in initially piercing simulated vein 141, but in avoiding contacting or piercing sidewall 141a after needle 210 is within simulated vein 141.

In the above-described embodiments, camera 121 is housed within housing 111 and positioned at the edge of simulated inner tissue 130. Various other positions and/or configurations of camera 121 may be employed in embodiments of the present disclosure. For example, FIG. 3A represents how camera 121 could be positioned within simulated inner tissue 130. In such embodiments, camera 121 could be placed in any suitable location within simulated inner tissue 130 and oriented towards the intended insertion area. For example, in FIG. 3A, camera 121 is positioned to the side of simulated vein 141 and captures a view that is perpendicular to the length of simulated vein. In other examples, camera 121 may be positioned above or below simulated vein 141 and may capture a view that aligns with the length of simulated vein 141. FIG. 3B provides an example where camera 121 is positioned within simulated vein 141. In such cases, camera 121 may be positioned upstream or downstream of the intended insertion area. In some embodiments, multiple cameras 121 may be used and may be positioned and/or oriented in a variety of ways to thereby capture a variety of views of the insertion area.

FIGS. 4A and 4B provide examples where vein simulator system 100 includes a sensor 400 that is contained in, on or adjacent to simulated vein 141. In FIG. 4A, sensor 400 may be in the form of a film that lines sidewall 141a, is embedded in sidewall 141a or is sufficiently near sidewall 141a to detect a change in an electrical property (e.g., capacitance) that a needle of a PIVC may invoke when it approaches or contacts the film. For example, sensor 400 could be a capacitive film that generates a signal that represents the proximity of the needle (e.g., by changing it capacitance relative to the proximity). Sensor 400 could provide such a signal to circuitry 401 of control system 120. Circuitry 401 could process the signal to determine the proximity of the needle and/or to determine when the needle has contacted sensor 400.

Control system 120 may include a feedback component 402 by which control system 120 outputs feedback. For example, feedback component 402 could be a speaker that outputs audio feedback. In such cases, circuitry 401 could cause feedback component 402 to output a sound when the signal from sensor 400 indicates that the needle has contacted sensor 400. Similarly, circuitry 401 could cause feedback component 402 to output a sound when the signal from sensor 400 indicates that the needle is approaching sensor 400 and may vary this sound (e.g., its pitch or volume) as the needle gets closer to sensor 400. The clinician can rely on such sound(s) to learn when the needle has reached the correct position for proper placement of the PIVC and/or to learn to avoid contacting sidewall 141a.

As another example, feedback component could be a visual feedback component such as one or more LEDs or even display device 160. In such cases, circuitry 401 could cause a visual feedback to be output to feedback component 402 to represent when the needle has contacted sensor 400 and/or to represent the current proximity of the needle to sensor 400. For example, if feedback component 402 is an LED, circuitry 401 could cause the LED to flash at quicker intervals as the needle approaches sensor 400. As another example, circuitry 401 could generate and update a visual representation of the needle's position relative to sidewall 141a based on the signal received from sensor 400 and provide the visual representation to feedback component 402 for display to the clinician (e.g., as part of a display incorporated into housing 111 or on display device 160). Any other reasonable type of feedback component could also be used.

FIG. 4B is a variation in which sensor 400 forms part of a circuit that is completed when the needle contacts sensor 400. In particular, the needle and sensor 400 may be connected to circuitry 401 which can detect when the needle contacts sensor 400 due to a change in current and/or voltage that this contact causes. In such embodiments, circuitry 401 may use feedback component 402 as described above to present feedback to the clinician.

In embodiments of the present disclosure, a vein simulator system may employ any one or more of the above-described types of sensors and feedback to assist a clinician in learning to properly place a PIVC. For example, in addition to camera 121, vein simulator system 100 may include sensor 400 to better notify the clinician when he or she contacts sidewall 141a.

In some embodiments, control system 120 may be configured to store the feedback that it generates so that it may be subsequently reviewed and/or scored. For example, control system 120 may maintain a log of a clinician's attempts to place a PIVC using vein simulator system 100. In such cases, control system 120 (or an external system) could use the log to create a score for the clinician. Such a score could represent whether each particular attempt was successful, an extent to which each particular attempt was successful, an average success rate, a success trend or any other measurement of success.

In embodiments where multiple sensors are employed, control system 120 may be configured to create associations between feedback from the different sensors. For example, control system 120 may employ a video time code to associate feedback from sensor 400 with the video. Such associations could enable the clinician to determine, while watching the video, exactly when the needle contacted the sidewall.

Although this disclosure provides an example where the vein simulator system resembles a human arm, the same techniques can be employed to create a vein simulator system resembling another portion of the human body such as a full arm, a leg, a torso, etc.

Because simulated skin 150 may be opaque, it may resemble human skin in that it prevents a clinician from seeing the PIVC while inserting it into simulated vein 141 or 142. Yet, because simulated inner tissue 130 can be transparent, the clinician may still rely on camera 121 to ensure that he or she is practicing the placement of the PIVC correctly. After a clinician has become confident that he or she can place a PIVC correctly, he or she may turn of camera 121 or otherwise avoid viewing the captured video to continue practicing. In this way, vein simulator system 100 can assist the clinician in quickly developing his or her skills while not becoming dependent on a video to perform proper PIVC placement.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed:

1. A vein simulator system comprising:
a base having a housing and a support, the housing extending above the support to form a wall that faces the support, the wall including an opening;
a simulated portion of a body positioned on the support, a first end of the simulated portion of the body being positioned against the wall to cover the opening, the simulated portion of the body including a first simulated vein and transparent simulated inner tissue through which the first simulated vein extends;
a control system positioned in the housing;
a first camera positioned in the opening in the wall of the housing and being directed towards the transparent simulated inner tissue to thereby capture video of the first simulated vein; and
a display device;
wherein the control system is configured to employ the first camera to capture video of the first simulated vein while a clinician attempts to place a catheter in the first simulated vein, and wherein the control system is configured to present the video to the clinician via the display device.

2. The vein simulator system of claim 1, wherein the simulated portion of the body is a simulated human arm.

3. The vein simulator system of claim 1, wherein the simulated portion of the body includes simulated skin, and wherein the simulated skin is secured overtop the transparent simulated inner tissue using screws that insert into holes in the support.

4. The vein simulator system of claim 3, further comprising:
securing members that are positioned overtop the simulated skin, the screws being tightened against the securing members to secure the simulated skin overtop the transparent simulated inner tissue.

5. The vein simulator system of claim 1, further comprising:
a second camera positioned inside the transparent simulated inner tissue.

6. The vein simulator system of claim 5, wherein the second camera is positioned to a side of the first simulated vein.

7. The vein simulator system of claim 5, wherein the second camera is positioned above or below the first simulated vein.

8. The vein simulator system of claim 1, wherein the support includes a channel in which a light source is positioned, the channel extending below the first simulated vein such that the light source illuminates the simulated inner tissue.

9. The vein simulator system of claim 8, wherein the control system causes the light source to flash based on feedback from one or more sensors positioned in the first simulated vein.

10. The vein simulator system of claim 1, further comprising:
a sensor in the form of a film that is on or forms part of a sidewall of the first simulated vein.

11. The vein simulator system of claim 10, wherein the control system creates feedback based on a signal created, induced or conveyed by the film in response to proximity or contact of a needle used to place the catheter, and wherein the feedback is presented on the display device.

12. The vein simulator system of claim 11, further comprising an audio feedback component.

13. The vein simulator system of claim 11, wherein the control system is configured to create an association between the feedback and the video.

14. A vein simulator system comprising:
a base having a housing and a support, the housing extending above the support to form a wall that faces the support, the wall including an opening;
a simulated portion of a body positioned on the support, a first end of the simulated portion of the body being positioned against the wall to cover the opening, the simulated portion of the body including a first simulated vein and transparent simulated inner tissue through which the first simulated vein extends;
a control system positioned in the housing:
a first camera positioned to capture video of the first simulated vein;
a first sensor that is contained in, on or adjacent to the first simulated vein, the first sensor being configured to provide to the control system an indication of when a needle contacts or is proximate to the first sensor during a clinician's placement of a catheter in the first simulated vein; and a display device;

wherein the control system is configured to employ the first camera to capture video of the first simulated vein during the clinician's placement of the catheter in the first simulated vein, and wherein the control system is configured to present the video to the clinician via the display device;

wherein the control system is configured to output feedback in conjunction with displaying the video, the feedback being based on the indication provided by the first sensor.

15. The vein simulator system of claim 14, wherein the first camera is one or more of:

positioned outside the transparent simulated inner tissue;

positioned inside the transparent simulated inner tissue; or positioned inside the first simulated vein.

16. The vein simulator system of claim 14, wherein the feedback is output audibly or visually.

17. The vein simulator system of claim 16, further comprising:

a light source that is positioned to illuminate the first simulated vein;

wherein the control system is configured to change a brightness of the light source in response to the feedback.

18. The vein simulator system of claim 14, wherein the first sensor and the needle are configured to complete a circuit when the needle contacts the first sensor.

19. A vein simulator system comprising:

a base having a housing and a support, the housing extending above the support to form a wall that faces the support, the wall including an opening;

a simulated portion of a body positioned on the support, a first end of the simulated portion of the body being positioned against the wall to cover the opening, the simulated portion of the body including a first simulated vein and transparent simulated inner tissue through which the first simulated vein extends;

a control system positioned in the housing;

a first camera positioned in the opening in the wall of the housing and being directed towards the transparent simulated inner tissue to thereby capture video of the first simulated vein;

a first sensor that is contained in, on or adjacent to the first simulated vein, the first sensor being configured to provide to the control system an indication of when a needle contacts or is proximate to the first sensor during a clinician's placement of a catheter in the first simulated vein; and a display device;

wherein the control system is configured to employ the first camera to capture video of the first simulated vein during the clinician's placement of the catheter in the first simulated vein, and wherein the control system is configured to present the video to the clinician via the display device;

wherein the control system is configured to output feedback in conjunction with displaying the video, the feedback being based on the indication provided by the first sensor.

20. The vein simulator system of claim 19, further comprising:

one or more additional cameras positioned within the transparent simulated inner tissue.

* * * * *